United States Patent [19]

Swim et al.

[11] Plant 4,666

[45] Mar. 10, 1981

[54] ROSE PLANT

[75] Inventors: Herbert C. Swim; Jack E. Christensen, both of Ontario, Calif.

[73] Assignee: Armstrong Nurseries, Inc., Ontario, Calif.

[21] Appl. No.: 87,804

[22] Filed: Oct. 24, 1979

[51] Int. Cl.[3] ..... A01H 5/00

[52] U.S. Cl. ..... Plt./24

[58] Field of Search ..... Plt./24

*Primary Examiner*—Robert E. Bagwill

*Attorney, Agent, or Firm*—William H. Elliott, Jr.; Andrew R. Klein

[57] ABSTRACT

A new variety of rose plant of the floribunda class, being a dwarf bush seedling, much branched and of moderately vigorous growth. Flowers are borne sometimes singly, sometimes three or more in irregular clusters on short to medium-length stems. The petal color, both inside and outside, is a bright golden yellow, fading at maturity to a lighter shade of the same color. The plant blooms profusely, with from 20 to 26 broad round petals on a plant of nearly ideal floribunda habit.

1 Drawing Figure

This invention relates to a new variety of rose plant, of the hybrid floribunda class. The plant is an outdoor seedling which is half hardy and of the dwarf bush type, cultivated for cut flowers and garden decoration. It was propagated by Herbert C. Swim and Jack E. Christensen in Ontario, Calif., having as its seed parent "Zorina" (U.S. Plant Pat. No. 2,321) and, as its pollen parent, "Golden Wave" (U.S. Plant Pat. No. 2,105). It holds its distinguishing characteristics through succeeding propagations by budding.

The new variety bears its flowers sometimes singly, but sometimes three or more to a stem, in irregular clusters on normal short to medium-length stems. The plant blooms freely to abundantly outdoors, and nearly continuously during the growing season. It has a moderate fragrance.

This new floribunda rose cultivar may be distinguished from its seed parent, Zorina, by the combination of the following characteristics:

Zorina bears grenadine-red flowers, whereas the new rose bears flowers of relatively uniform yellow coloration.

The new cultivar has significantly larger flowers of 3½ to 4½ inches in diameter, whereas Zorina has flowers of 3 inches in diameter.

Zorina is adapted primarily to greenhouse cut rose use, whereas the new rose is adapted primarily to garden use.

This new floribunda rose cultivar may be distinguished from its pollen parent, Golden Wave, by the combination of the following characteristics:

Golden Wave bears flowers of significantly deeper yellow coloration than the flowers of the new cultivar.

Golden Wave is adapted primarily to greenhouse cut rose use, whereas the new rose is adapted primarily to garden use.

The new cultivar is classed as a hybrid floribunda rose, whereas Golden Wave is classed as a hybrid tea rose.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is erect and of average length and average caliper, with some small stipitate glands. The color is between Strong Yellow Green, 2.5GY6/8, and Moderate Yellow Green, 2.5GY5/5.

Before the calyx breaks, the bud is small and pointed-ovoid in form, with narrow foliaceous appendages on the surface of the bud. Usually, slender foliaceous parts extend beyond the tip of the bud equal to one-half or more of its length.

As the calyx breaks, the color is between Strong Greenish Yellow, 10Y8/11, and Brilliant Yellow Green, 2.5GY8/9. The inner surface of the sepals has a fine tomentum; margins of the sepals are lined with stipitate glands and hairs.

As the first petal opens, the bud is average to large in size, of medium length and pointed. The color on the outside of the petal is between Vivid Yellow, 2.5Y8/12, and Brilliant Yellow, 2.5Y9/9. The inside surface of the petal shows a color which is between Vivid Yellow, 2.5Y8/12, and Vivid Yellow, 5Y8/12. The bud opens up well and is not prevented from opening by cold, hot, wet or dry weather.

BLOOM

The size of the bloom when fully open is average to large, ranging from 3½ inches to 4½ inches. The petalage is double, with from 20 to 26 petals plus from 0 to 4 petaloids, arranged regularly. The bloom is high centered at first, becoming cupped to high centered. At first the petals remain tightly cupped, with tips reflexed slightly outward, becoming later at maturity more loosely cupped, with tips reflexed outward.

The petals are of medium thickness, with inside slightly velvety and outside slightly shiny to satiny. The outside petals are round in shape, while both the intermediate and inside petals are nearly round. The colors may be modified by being striped, blotched, shaded and/or washed with other colors.

The following paragraph describes color values observed in a flower newly opened in the month of November. The plant had been grown outdoors, in Ontario, Calif.

The outer surface of the outside petal was between Vivid Yellow, 2.5Y8/12, and Brilliant Yellow, 2.5Y9/9. The outer surfaces of the intermediate and inside petals were similarly colored. The inner surface of the outside petal was between Vivid Yellow, 5Y8/12, and Brilliant Yellow, 5Y9/9. The inner surfaces of the intermediate and inside petals were similarly colored.

The following paragraph describes color values observed in a bloom which had been open for three days, indoors, in the month of November. The plant had been grown in Ontario, Calif.

The outer surface of the outside petal was lighter than a shade near Brilliant Yellow, 5Y9/9, in color. The inner surface showed the same coloration as the outer surface. The same color values characterized the inside petals.

The general color effect of the newly opened flower is near Brilliant Yellow, 2.5Y9/9. The bloom after being three days open gives a general color effect of being lighter than a shade near Brilliant Yellow, 5Y9/9. Some petals and/or petaloids persist, but most drop off cleanly.

The flowers on the bush in the garden persist for from three to five days in the month of November, in the locality named. Cut roses grown outdoors and kept at living-room temperatures will last from three to five days in the month of November.

REPRODUCTIVE ORGANS

There are many stamens arranged regularly about the pistils.

Filaments are medium length to long, most with anthers.

The anthers are medium size to large, all opening approximately at once. The color of the margins is near Dark Orange Yellow, 7.5YR6/9. The color near the point of attachment of the filament is near Brilliant Yellow, 5Y9/9.

Pollen is from moderate to abundant and near Strong Orange, 5YR7/11, in color.

The pistils are approximately 100 in number, which is average.

The styles are uneven, average length, thin to average in caliper, and loosely bunched. The color is near Brilliant Yellow Green, 2.5GY9/8.

The stigma is near Brilliant Greenish Yellow, 10Y9/9, in color.

Most of the ovaries are usually enclosed in the calyx.

Since this variety does not normally produce hips when grown outdoors in the locality named, there were no hips or seeds for description.

FOLIAGE

The compound leaves usually comprise three to seven leaflets. They are abundant, medium size, moderately heavy and semi-glossy. The leaflets are ovate, with apex acute, base obtuse, and margin irregularly serrate.

The mature foliage displays on its upper surface a coloration between Grayish Olive Green, 5GY3/2, and Moderate yellow Green, 5GY5/6. The under surface is more or less near Moderate Yellow Green, 2.5GY5/5, heavily overlaid with a grayish bloom.

The young foliage on its upper surface is darker than Dark Red, 5R3/7, in color. The under surface is slightly darker than Dark Red, 2.5R3/7.

The rachis is of average size. The upper side is grooved, with some stipitate glands on the edges, while the under side is sparsely prickly.

The stipules are medium-length, moderately narrow, with medium-length points turning out at an angle of less than 90°.

The plant displays a more than average resistance to mildew, compared to other commercial varieties grown in the locality named under comparable conditions.

GROWTH

The plant is of bushy habit and much branched. It displays a moderately vigorous growth. The canes are of medium caliper.

The main stems are between Light Olive, 10Y5/5, and Moderate Olive, 10Y4/3, in color, with a light gray bloom. They bear a few large prickles which are medium-length, hooked slightly downward, with medium-length, moderately narrow base. They are a color between Strong Brown, 5YR4/5, and Moderate Brown, 7.5YR4/5, with heavy gray bloom. There are no small prickles and no hairs.

The branches are near Strong Yellow Green, 5GY7/10, in color, with a slight gray bloom. They carry a few large prickles which are medium-length, hooked slightly downward, and with medium-length, moderately narrow base. They are a color at the base which is near Strong Red, 5R4/12, with the point being near Brilliant Yellow Green, 2.5GY9/8. There are no small prickles and no hairs.

New shoots have a color between Strong Yellow Green, 5GY6/8, and Moderate Yellow Green, 5GY5/6, moderately overlaid with near Dark Red, 2.5R3/7. They carry several large prickles which are medium-length, almost straight to hooked slightly downward, with medium-length, moderately narrow base. At the base, the color is near Strong Red, 5R4/12, while the point is near Brilliant Yellow Green, 2.5GY9/8. There are no small prickles and no hairs.

We claim:

1. A new and distinct variety of rose plant of the floribunda class, substantially as herein shown and described, and being particularly characterized by the brilliant golden yellow color of its blooms, the buds and flowers being well-formed and relatively large, with 20 to 26 broad round petals, blooming profusely substantially throughout the growing season.

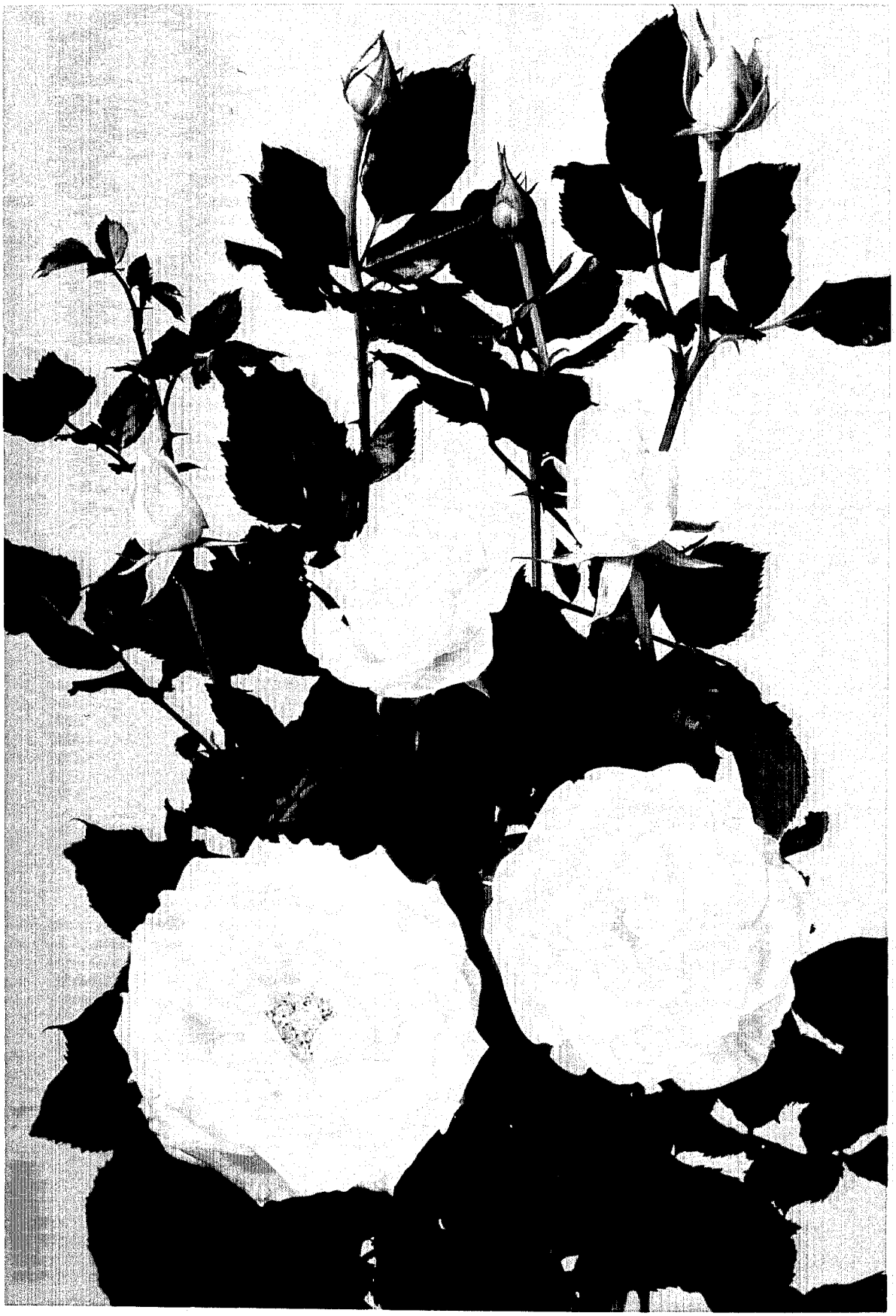

* * * * *